United States Patent
Davenport et al.

(10) Patent No.: US 9,395,246 B2
(45) Date of Patent: Jul. 19, 2016

(54) GAS ANALYSER

(71) Applicant: ALPHASENSE LIMITED, Braintree, Essex (GB)

(72) Inventors: John Davenport, Cranfield (GB); Elizabeth Jane Hodgkinson, Cranfield (GB); John Robert Saffell, Braintree (GB); Ralph Peter Tatam, Cranfield (GB)

(73) Assignee: ALPHASENSE LIMITED, Braintree (GB)

( * ) Notice: Subject to any disclaimer, the term of this patent is extended or adjusted under 35 U.S.C. 154(b) by 84 days.

(21) Appl. No.: 13/955,479

(22) Filed: Jul. 31, 2013

(65) Prior Publication Data

US 2014/0034840 A1 Feb. 6, 2014

(30) Foreign Application Priority Data

Jul. 31, 2012 (GB) .................................. 1213637.0
Jul. 31, 2012 (GB) .................................. 1213640.4

(51) Int. Cl.
*G01N 21/33* (2006.01)
*G01J 3/42* (2006.01)
*G01N 21/31* (2006.01)
*G01N 21/05* (2006.01)

(52) U.S. Cl.
CPC .................. *G01J 3/42* (2013.01); *G01N 21/314* (2013.01); *G01N 21/33* (2013.01); *G01N 21/05* (2013.01)

(58) Field of Classification Search
CPC .............................. G01N 21/33; G01N 21/05
See application file for complete search history.

(56) References Cited

U.S. PATENT DOCUMENTS

| 4,835,393 A | 5/1989 | Krauss |
| 5,070,246 A * | 12/1991 | Durham et al. ............... 250/373 |
| 5,132,227 A | 7/1992 | Kelly |
| 5,272,345 A | 12/1993 | Durham et al. |
| 6,455,851 B1 | 9/2002 | Lord et al. |
| 2001/0055441 A1 * | 12/2001 | MacKinnon .................... 385/16 |
| 2011/0096332 A1 | 4/2011 | Bugge |
| 2011/0211193 A1 | 9/2011 | Saveliev et al. |

FOREIGN PATENT DOCUMENTS

| CN | 102410986 | 4/2012 |
| EP | 0 254 879 | 2/1988 |

(Continued)

OTHER PUBLICATIONS

Kudo et al., Biochemical gas sensor (bio-sniffer) for ultrahigh-sensitive gaseous formaldehyde monitoring, Aug. 1, 2010, Biosensors and Bioelectronics, vol. 26, pp. 854-858.*

(Continued)

*Primary Examiner* — Christine Sung
(74) *Attorney, Agent, or Firm* — Nixon & Vanderhye P.C.

(57) ABSTRACT

A gas analyzer and a corresponding method is provided to measure the concentration of formaldehyde within enclosed environments such as within buildings comprising an ultraviolet light source, a sample chamber, a detector. The detector measures the intensity of light received by photosensors within a measurement range of wavelengths, and at least one reference range of wavelengths. Advantageously, the concentration of formaldehyde is determined taking into account fluctuations in the intensity of light emitted by the light source, and in the presence of any interferents such as nitrogen dioxide.

20 Claims, 10 Drawing Sheets

(56) References Cited

FOREIGN PATENT DOCUMENTS

| | | |
|---|---|---|
| GB | 2 117 112 | 10/1983 |
| JP | 2000-241313 | 9/2000 |
| WO | WO 91/04470 | 4/1991 |
| WO | WO 95/10037 | 4/1995 |
| WO | WO 98/30897 | 7/1998 |
| WO | WO 99/05508 | 2/1999 |
| WO | WO 01/13091 | 2/2001 |
| WO | WO 2004/017054 | 2/2004 |

OTHER PUBLICATIONS

Pope et al., High-resolution absorption cross sections of formaldehyde at wavelengths from 313 to 320 nm, Nov. 15, 2004, Pub. Chem. Chem. Phys.,vol. 1, pp. 79-84.*
J. Davenport, "UV Spectroscopic Instrumentation for Formaldehyde Detection in the Indoor Environment", Cranfield University Doctoral Thesis, Submitted Jan. 2014, 242 pages.
M. Hausmann, U. Brandenburger, T. Brauers and H-P Dorn, "Simple Monte Carlo methods to estimate the spectra evaluation error in differential-optical-absorption spectroscopy", Applied Optics, vol. 38, No. 3, pp. 462-475, Jan. 1999.
G. Dooly, C. Fitzpatrick and E. Lewis, "Deep UV based DOAS system for the monitoring of nitric oxide using ratiometric separation techniques", Sensors and Actuators B: Chemical, vol. 134, pp. 317-323, 2008.
C. J. Weschler, "Changes in indoor pollutants since the 1950s," Atmospheric Environment, vol. 43, pp. 153-169, 2009.
A. Wisthaler, G. Tamas, D. P. Wyon, P. Strom-Tejsen, D. B. J. Space, A. Hansel, T. D. Mark and W. C. J., "Products of Ozone-Initiated Chemistry in a Simulated Aircraft Environment," Environmental Science and Technology, vol. 39, pp. 4823-4832, 2005.
J. Nøjgaard, A. Nørgaard and P. Wolkoff, "On-line analysis of secondary oxonides from cyclohexane and D-limonene ozonolysis using atmospheric sampling townsend discharge ionization mass spectrometry," Atmospheric Environment, vol. 41, pp. 8345-8354, 2007.
R. Pal and K. Kim, "Gas chromatographic approach for the determination of carbonyl compounds in ambient air," Microchemical Journal, vol. 90, p. 147-158, 2008.
H. Bagheri, M. Ghambarian, A. Salemi and A. Es-Haghi, "Trace determination of free formaldehyde in DTP and DT vaccines and diphtheria-tetanus antigen by single drop microextraction and gas chromatography—mass spectrometry," vol. 50, p. 287-292, 2009.
K. A. Ramazan, D. Syomin and B. J. Finlayson-Pitts, "The photochemical production of HONO during the heterogeneous hydrolysis of NO," Physical Chemistry Chemical Physics, vol. 6, pp. 3836-3843, 2004.
M. Sorgel, I. Trebs, A. Serafimovich, A. Moravek, A. Held and C. Zetzsch, "Simultaneous HONO measurements in and above a forest canopy: influence of turbulent exchange on mixing ratio differences," Atmospheric Chemistry and Physics, vol. 11, p. 841-855, 2011.
S. S. Park, J. H. Hong, J. H. Lee, Y. J. Kim, S. Y. Cho and S. J. Kim, "Investigation of nitrous acid concentration in an indoor environment using an in-situ monitoring system," Atmospheric Environment, vol. 42, p. 6586-6596, 2008.
T. Salthammer, S. Mentese and R. Marutzky, "Formaldehyde in the Indoor Environment," Chemical Reviews, vol. 110, p. 2536-2572, 2010.
R. A. Rudel and L. J. Perovich, "Endocrine disrupting chemicals in indoor and outdoor air," Atmospheric Environment, vol. 43, pp. 170-181, 2009.
G. J. Raw, S. K. D. Coward, V. M. Brown and D. R. Crump, "Exposure to air pollutants in English homes," Journal of Exposure Analysis and Environmental Epidemiology, vol. 14, p. S85-S94, 2004.
F. H. Shair and K. L. Heitner, "Theoretical model for relating indoor pollutant," Environmental Science and Technology, vol. 8, p. 444-451, 1974.
J. A. Mott, M. I. Wolfe, C. J. Alverson, C. S. Macdonald, C. R. Bailey, L. B. Ball, J. E. Moorman, J. H. Somers, D. M. Mannino and S. C. Redd, "National vehicle emissions policies and practices and declining U.S. carbon monoxide-related mortality," JAMA—Journal of the American Medical Association, vol. 288, p. 987-989, 1974, reprinted 2002.
J. London and J. Kelly, "Global trends in total atmospheric ozone," Science, vol. 184, p. 987-989, 1974.
P. Wolkoff, "Volatile organic compounds—sources, measurements, emissions, and the impact on indoor air quality. Indoor Air," Indoor Air, vol. 5, No. 53, pp. 5-73, 1995.
S. K. Brown, M. R. Sinn, M. J. Abramson and C. N. Gray, "Concentrations of volatile organic compounds in indoor air—a review." Indoor Air, vol. 4, pp. 123-134, 1994.
A. T. Hodgson and H. Levin, "Volatile organic compounds in indoor air: a review of concentrations measured in North America since 1990," Lawrence Berkeley National Lab Report, LBNL-51715, 2003 (31 pages).
N. T. Program, Report on Carcinogens, U.S. Department of Health and Human Services, Public Health Service, Washington, DC,: 2005, 11th ed. (507 pages).
Y. Xu and J. C. Little, "Predicting emissions of SVOCs from polymeric materials and their interaction with airborne particles," Environmental Science and Technology, vol. 40, p. 456-461, 2006.
C. J. Weschler and W. W. Nazaroff, "Semivolatile organic compounds in indoor environments, " Atmospheric Environment, vol. 42, p. 9018-9040, 2008.
Executive Summary: Third Executive Summary: Third National Report on Human Exposure to Environmental Chemicals, Atlanta, GA: CDC (Centers for Disease Control and Prevention), 2005 (475 pages).
E. Abt, H. H. Suh, P. Catalano and P. Koutrakis, "Relative contribution of outdoor and indoor particle sources to indoor concentrations," Environmental Science and Technology, vol. 34, p. 3579-3587, 2000.
K. Davitt, Y. K. Song, A. V. Nurmikko, S. R. Jeon, M. Gherasimova, J. Han, Y. L. Pan and R. K. Chang, "UV LED arrays for spectroscopic fingerprinting of airborne biological particles," Current Topics in Solid State Physics, vol. 2, No. 7, p. 2878-2881, 2005.
K. Davitt, Y.-K. Song, W. R. P, III and A. V. Nurmikko, "290 and 340 nm UV LED arrays for fluorescence detection from single airborne particles," Optics Express, vol. 13, No. 23, pp. 9548-9555, 2005.
W. J. Chaplin, Y. Elsworth, G. R. Isaak, B. A. Miller, R. New and B. Pinter, "Noise characteristics of full-disc helioseismic observations made by resonant scattering spectrometers," Monthly Notices of the Royal Astronomical Society, vol. 359, No. 2, pp. 607-614, 2005.
K. Bogumil, J. Orphal, T. Homann, S. Voigt, P. Spietz, O. C. Fleischmann, A. Vogel, M. Hartmann, H. Kromminga, H. Bovensrnann, J. Frerick and J. P. Burrows, "Measurements of molecular absorption spectra with the SCIAMACHY pre-flight model: instrument characterization and reference data for atmospheric remote-sensing in the 230-2380 nm region," Journal of Photochemistry and Photobiology A: Chemistry, vol. 157, pp. 167-184, 2003.
B. A. Thompson, P. Harteck and R. R, Reeves Jr., "Ultraviolet absorption coefficients of $CO_2$, CO, $H_2O$, $N_20$, $NH_3$, NO, $SO_2$, and $CH_4$ between 1850 and 4000 A," Journal of Geophysical Research, vol. 68, No. 24, pp. 6431-6436, 1963.
A. C. Vandaele, C. Hermans and S. Fally, "Fourier transform measurements of $SO_2$ absorption cross-sections: II. Temperaturre dependence in the 29000-44000/cm (227-345nm) region," Journal of Quantitative Spectroscopy & Radiative Transfer, vol. 110, pp. 2115-2126, 2009.
R. Meller and G. K. Moortgat, "Temperature dependence of the absorption cross sections of formaldehyde between 223 and 323 K in the wavelength range 225-375 nm," Journal of Geophysical Research-Atmospheres, vol. 105, No. D6, pp. 7089-7101, 2000.
W. Schneider, G. K. Moortgat, G. S. Tyndall and J. P. Burrows, "Absorption cross-sections of $NO_2$ in the UV and visible region (200-700nm) at 298 K," Journal of Photochemistry and Photobiology. A: Chemistry, vol. 40, pp. 195-217, 1987.
J. Magneron, R. Thevenet, A. Mellouki and G. Le Bras, "A Study of the Photolysis and OH-initiated Oxidation of Acrolein and trans-Crotonaldehyde," Journal of Physical Chemistry A, vol. 106, pp. 2526-2537, 2002.

(56) References Cited

OTHER PUBLICATIONS

A. Fahr and A. K. Nayak, "Temperature dependent ultraviolet absorption cross sections of 1,3-butadiene and butadiyne," Chemical Physics, vol. 189, pp. 725-731, 1994.

H. R. Cooper and H. W. Melville, "The Kinetics of the Autoxidation of n-Decanal. Part I. The Mechanism of Reaction," Journal of the Chemical Society, pp. 1984-1993, 1951.

J. W. Au, G. Cooper, G. R. Burton, T. N. Olney and C. E. Brion, "The valence shell photoabsorption of the linear alkanes, CnH2n+2 ( n = 1-8 ): absolute oscillator strengths ( 7-220 eV )," Chemical Physics, vol. 173, pp. 209-239, 1993.

A. Bolovinos, J. Philis, E. Pantos, P. Tsekeris and G. Andritsopoulos, "The Methylebertzenes vis-a-vis Benzene," Journal of Molecular Spectroscopy, vol. 94, pp. 55-68, 1982.

A. Bolovinos, J. Philis, P. E., P. Tsekeris and G. Andritsopoulos, "The methylebenzenes vis-a-vis benzene—comparison of their spectra in the Rydberg series region," Journal of Chemical Physics, vol. 75, pp. 4343-4349, 1981.

W. Koban, J. D. Koch, R. K. Hanson and C. Schulz, "Absorption and fluorescence of toluene vapor at elevated temperatures," Physical Chemistry Chemical Physics, vol. 6, pp. 2940-2945, 2004.

T. Etzkorn, B. Klotz, S. Sorensen, I. V. Patroescu, I. Barnes, K. H. Becker and U. Platt, "Gas-phase absorption cross sections of 24 monocyclic aromatic hydrocarbons in the UV and IR spectral ranges," Atmospheric Environment, vol. 33, pp. 525-540, 1999.

D. Kubala, E. A, Drage, A. M. E. Al-Faydhi, J. Kocisek, P. Papp, V. Matejcik, P. Mach, J. Urban, P. Limäo-Vieira, S. V. Hoffmann, S. Matejcik and N. J. Mason, "Electron impact ionisation and UV absorption study of alpha- and beta-pinene," International Journal of Mass Spectrometry, vol. 280, pp. 169-173, 2009.

P. C. Simon, D. Gillotay, N. Vanlaethemmeuree and J. Wisemberg, "Temperature-dependence of ultraviolet-absorption cross-section of chlorofluoroethanes," Annales Geophysicae-Atmospheres Hydrospheres and Space Sciences, vol. 6, pp. 239-247, 1988.

H. Z. C. Scharping, Substituent effects in the VUV absorption-spectra of monochlorobenzene and ortho-dichlorobenzene, meta-dichlorobenzene and para-dichlorobenzene, Journal of Molecular Spectroscopy: vol. 112, Issue 1, pp. 8-17, 1985.

J. W. Au, G. R. Burton and C. E. Brion, "Quantitative spectroscopic studies of the valence-shell electronic excitation of Freons (CFC13, CF2C12, CF3C1 and CF 4) in the VUV and soft X-ray regions," Chemical Physics, vol. 221, pp. 151-168, 1997.

C. Hubrich, C. Zetzsch and F. Stahl, "Absorption-spectra of halogenated methanes in wavelength refion from 275 to 160 nm at temperatures of 298 and 208 K," Berichte der Bunden-Gesellschaft-Physical Chemistry Chemical Physics, vol. 81, pp. 437-442, 1977.

J. Doucet, P. Sauvageau and C. Sandorfy, "Photoelectron and far Ultravoplet absorption-spectra of chlorofluoro derivatives of ethane," Journal of Chemical Physics, vol. 62, pp. 355-359, 1975.

Li Guankun et al: "Measurement of atmospheric formaldehyde profiles with a laser-induced fluorescence lidar", Laser Radar Technology and Applications XVII, SPIE, 1000 20$^{th}$ St. Bellingham WA 98225-6705 USA, vol. 8379, No. 1, May 11, 2012, pp. 1-11, XP060003285.

Jochen Stutz and Ulrich Platt "Numerical analysis and estimation of the statistical error of differential optical absorption spectroscopy measurements with least-squares methods", Applied Optics, vol. 35, No. 30, Oct. 1996.

U. Platt, Differential Optical Absorption Spectroscopy, Chapter 2 of Air Monitoring by Spectroscopic Techniques, edited by M Sigrist, pp. 27-84, 1994 (58 pgs.).

* cited by examiner

GAS ANALYSER

CROSS REFERENCE TO RELATED APPLICATIONS

This application is based upon and claims the benefit of priority from UK Patent Application No. 1213640.4, filed on 31 Jul. 2012 and UK Patent Application No. 1213637.0, filed on 31 Jul. 2012; the entire contents of which are incorporated herein by reference.

FIELD OF THE INVENTION

The invention relates to the field of gas sensors and gas analysers, and with particular reference to the field of formaldehyde gas analysers for use within enclosed environments.

BACKGROUND TO THE INVENTION

Formaldehyde, also known as methanal or methyl aldehyde, is an industrially important chemical, used predominantly in the manufacture of resins, such as urea formaldehyde resin and melamine resin, for example. Formaldehyde resins are used as adhesives and in the production of paints and wallpapers.

During the lifetime of a product that incorporates a formaldehyde resin, the resin may break down to release formaldehyde gas into the surrounding environment. Where the products are installed or used within a confined space such as those found within domestic residences or offices, or where the products are stored and/or transported in shipping containers, the resulting concentration of formaldehyde can exceed safe limits. Formaldehyde gas is toxic, allergenic and carcinogenic and can be dangerous at concentrations as low as 100 parts-per-billion (ppb). For example, the World Health Organisation (WHO) guideline level for prolonged formaldehyde exposure is 80 ppb, and this guideline has been adopted by many countries.

Therefore, it is essential to be able to detect the presence of formaldehyde in confined spaces such as those found in buildings or containers before the concentration of formaldehyde reaches dangerous levels.

Gas sensors known in the art to detect formaldehyde include gas chromatography and optical absorption spectroscopy.

Gas chromatography mixes a gas sample with a carrier gas (such as helium or nitrogen) and which is then passed through a long cylindrical column filled with material that the gas sample must migrate through. The components of the gas sample are separated out by the time it takes each component to reach the detector. Gas chromatography can be highly accurate and reliable. However, samples take a long time to pass through the column (several hours) and must be injected into the column, making it impossible to use for continuous real-time measurements.

Optical absorption spectroscopy techniques can be employed to detect formaldehyde by measuring the absorption of light in the specific range of wavelengths absorbed by formaldehyde (250 nm to 360 nm). For example, differential optical absorption spectroscopy uses high resolution spectrometers and differential post-measurement analysis to identify narrow band features within absorption spectra. However, complex processing of the spectral data is required to separate out the target analyte signal (formaldehyde in this case) from the background of other trace chemicals that absorb light in the same region of the spectrum. In addition, high resolution spectrometers are expensive and make any gas sensor using this technique correspondingly expensive.

A further complication for the measurement of formaldehyde within enclosed environments such as those found within a building is the presence of other gaseous species that also absorb light within the same region of the spectrum as formaldehyde. For example, decanal, hexanal, acetaldehyde, ozone, nitrogen dioxide and sulphur dioxide all absorb light within the range of 240 nm to 360 nm, which encompasses the absorption band for formaldehyde.

Therefore, it is particularly difficult and impractical to measure the concentration of formaldehyde in enclosed environments such as those found within buildings using standard optical absorption techniques due to the presence of the wide variety of species present that absorb light within a similar range of wavelengths as formaldehyde.

Therefore, one aim of the present invention is to provide an affordable gas sensor capable of real-time continuous measurement of formaldehyde concentrations in enclosed environments such as those found within buildings.

Typical optical absorption gas sensors use two detectors to provide a measurement signal and a calibration signal that compensates for any variation in performance of the light source. For example, it is well known for gas sensors to use a single light source, to split the light that has passed through a sample between two detectors using a beam splitter and to then select a different wavelength or band of wavelengths for each detector using a filter. However, each optical component adds to the expense of the gas sensor and to the attenuation of light that reaches each sensor, leading to a loss of sensitivity.

Accordingly, a further aim of the invention is to provide an improved gas sensor that is cheap and has a high sensitivity to a target analyte such as formaldehyde.

Furthermore, the optical components of gas sensors are very sensitive to the wavelength of light used. When the temperature of these optical components changes, their wavelength characteristics also change. For example, the range of wavelengths that are transmitted by a filter component such as a band-pass filter, for example, may vary with temperature.

The invention further aims to provide a method of calibrating a gas sensor to account for thermal fluctuations.

SUMMARY OF THE INVENTION

According to a first aspect of the invention there is provided a gas analyser for measuring the concentration of formaldehyde in ambient air within an enclosed environment, the gas analyser comprising a sample chamber in gaseous communication with ambient air, at least one ultraviolet light source, a detector configured to receive ultraviolet light emitted by the at least one ultraviolet light source and passed through the sample chamber, and a processor, the detector comprising at least one photosensor sensitive to ultraviolet light emitted by the at least one ultraviolet light source and operable to produce a plurality of measured ultraviolet light signals indicative of sensed ultraviolet light in each of a plurality of wavelength bands, the plurality of measured ultraviolet light signals including at least a first measured ultraviolet light signal indicative of sensed ultraviolet light in at least some of a measurement range of 337.5 nm to 346 nm or 325 nm to 332 nm, and a second said measured ultraviolet light signal indicative of sensed ultraviolet light in at least some of a reference range of 332 nm to 337 nm, 347 nm to 350 nm or 356 nm to 370 nm, wherein the processor is configured (e.g. programmed) to generate a measurement output signal indicative of the concentration of formaldehyde in ambient air taking into account the first and second measured ultraviolet light signals and at least one further signal which is dependent on the concentration of nitrogen dioxide in ambient air and at least partially independent of the first and second measured ultraviolet light signals.

We have found that, surprisingly, there are narrow wavelength ranges from 337.5 nm to 346 nm and from 325 nm to 332 at which formaldehyde absorbs ultraviolet light which can be used to measure formaldehyde despite the presence of common indoor inteferents provided that a reference measurement is made in at least one of the wavelength ranges 332 nm to 337 nm, 347 nm to 350 nm and 356 nm to 370 nm, and provided that a further measurement is taken which allows for absorption by nitrogen dioxide to be allowed for. The reference measurement (the second measured ultraviolet light signal) is used to calibrate for the intensity of the ultraviolet light being received at the detector, which can vary significantly, for example with temperature and over time.

This is possible because, within these ranges, the absorption from the following common interferents found in ambient air within enclosed environments such as those within buildings is sufficiently low at these wavelength ranges to have only a small effect on the accuracy of the measurement: acetaldehyde, ethylbenzene, hexanal, ozone, decanal, dibutlyphthalate, sulphur dioxide, toluene, dichlorodiphenyltrichloroethane (DDT) and triphenylphosphate. Nitrogen dioxide does still absorb strongly at these wavelengths, but it can be corrected for by way of a further measurement. This might be a further optical absorption measurement or could be obtained using a separate nitrogen dioxide sensor. Nitrogen dioxide sensors are relatively cheap and provide independent measurements of nitrogen dioxide concentration. The nitrogen dioxide sensor might be an electrochemical nitrogen dioxide sensor. Accordingly the invention extends to a gas analyser further comprising a nitrogen dioxide sensor in gaseous communication with ambient air and wherein the further signal is an output of the nitrogen dioxide sensor representative of the concentration of nitrogen dioxide in ambient air.

However, a further signal which is dependent on the concentration of nitrogen dioxide in ambient air and at least partially independent of the first and second measured ultraviolet light signals can be obtained from a third said measured ultraviolet light signal indicative of sensed ultraviolet light in at least some of a further one of the reference ranges of 332 nm to 337 nm, 347 nm to 350 nm or 356 nm to 370 nm. That is to say, the second measured ultraviolet light signal is indicative of sensed light in at least some of one of the reference ranges of 332 nm to 337 nm, 347 nm to 350 nm or 356 nm to 370 nm and the third measured ultraviolet light signal is indicative of sensed light in at least some of a second one of the reference ranges of 332 nm to 337 nm, 347 nm to 350 nm or 356 nm to 370 nm When a said third measured ultraviolet light signal is also taken into account the processor now has three at least partially independent inputs, which provide three degrees of freedom, enabling the intensity of ultraviolet light being received by the detector, the absorption of ultraviolet light by formaldehyde and the absorption of ultraviolet light by nitrogen dioxide to be independently measured.

The enclosed environment may be the inside of a building, such as within offices, domestic residences or warehouses, for example. Alternatively, the enclosed environment may be inside a container such as those within which products are stored and/or transported for long periods of time, for example. The gas analyser may measure only formaldehyde (subject to any interference) or may measure formaldehyde and one or more other gaseous analytes.

We say that the respective measured ultraviolet light signals are indicative of sensed ultraviolet light in at least some of respective wavelength ranges as, although measurement of received light across the whole of the respective ranges (337.5 nm to 346 nm or 325 nm to 332 nm for measurement; 332 nm to 337 nm, 347 nm to 350 nm or 356 nm to 370 nm for reference) is typically measured, it would be possible to measure only ultraviolet light received by the detector within part (e.g. at least 10% of or at least 50% of) the respective ranges.

It may be that the processor takes into account one or more ultraviolet light signals indicative of sensed ultraviolet light in at least some of both the measurement range of 337.5 nm to 346 nm and the measurement range of 325 nm to 332 nm. If the processor takes into account an ultraviolet light signal indicative of sensed ultraviolet light in only one of at least some of the measurement range of 337.5 nm to 346 nm and at least some of the measurement range of 325 nm to 332 nm, at least some of the measurement range of 337.5 nm to 346 nm is preferred. Therefore, it may be that the first measured ultraviolet light signal is indicative of sensed ultraviolet light in at least some of the measurement range of 337.5 nm to 346 nm and none of the range of 325 nm to 332 nm.

It may be that the second measured ultraviolet light signal is indicative of sensed ultraviolet light in at least some of only one of the reference ranges of 332 nm to 337 nm, 347 nm to 350 nm or 356 nm to 370 nm. In this case, the reference range from 332 nm to 337 nm is preferred, although the others could be used. It may be that the second measured ultraviolet light signal is indicative of sensed ultraviolet light in at least some of the reference range of 332 nm to 337 nm and wherein the processor does not use as a reference any measured ultraviolet light signal indicative of sensed ultraviolet light in the range of 347 nm to 350 nm or 356 nm to 370 nm.

In embodiments where a third measured ultraviolet light signal is taken into account, typically the second measured ultraviolet light signal is indicative of sensed ultraviolet light in at least some of a reference range of 332 nm to 337 nm and the third measured ultraviolet light signal is indicative of sensed ultraviolet light in at least some of the reference range of 347 nm to 350 nm, but either one of the reference ranges could instead be indicative of sensed ultraviolet light in a reference range from 356 nm to 370 nm.

Although it can help with data processing for the processor to receive measured ultraviolet light signals indicative of sensed ultraviolet light in each of the reference bands, a simpler and more cost effective gas analyser can be built if only ultraviolet light in selected measurement and reference bands is measured and taken into account.

It may be that the detector comprises a photosensor which is used to measure ultraviolet light received in a plurality of different wavelength ranges and which generates at least the first and second measured ultraviolet light signals, for example, by directing ultraviolet light from the at least one light source, which has a wavelength range which changes with time (e.g. changes periodically between a said measurement wavelength range and a said reference range) through the sample chamber onto the detector. This could be achieved with an ultraviolet light source which has a variable wavelength output or by using a plurality of ultraviolet light sources which generate ultraviolet light at a plurality of different wavelength ranges.

In order to obtain first and second measured ultraviolet light signals indicative of ultraviolet light received in different wavelength bands it may be that the detector comprises a plurality of photosensors, each of which receives ultraviolet light of a different range of wavelengths and the first and second measured ultraviolet light signals (and the third measure ultraviolet light signal, where present) are each generated by different photosensors which receive ultraviolet light of a different range of wavelengths.

Preferably, the detector comprises a dispersive optical element and a linear array of photosensors (e.g. photodiodes) configured so that ultraviolet light from the at least one ultraviolet light source is separated by wavelength by the dispersive optical element and directed onto the linear array of photosensors such that each photosensor receives ultraviolet light at a different range of wavelengths. The different range of wavelengths are typically non-overlapping but this is not essential. Each photosensor typically generates a respective measured ultraviolet light signal.

It is not essential that each measurement range of wavelengths or each reference range of wavelengths falls only on a single photosensor. A plurality of first measured ultraviolet light signals may be generated by a respective plurality of photosensors and processed by the processor. A plurality of second measured ultraviolet light signals may be generated by a respective plurality of photosensors and processed by the processer. A plurality of third measured ultraviolet light signals may be generated by a respective plurality of photosensors and processed by the processer.

Similarly, it may be that a photosensor which generates the first measured ultraviolet light signal, second measured ultraviolet light signal or third measured ultraviolet light signal (where present) receives ultraviolet light in at least some of a said measurement range of wavelengths and at least some of a said reference range of wavelengths, provided that the proportion of ultraviolet light in the measurement and reference ranges of wavelengths is different for each photosensor so that the first, second and third measured ultraviolet signals are at least in part independent.

Typically, the linear array of photosensors comprises fewer than 20 photosensors. Preferably, the linear array of photosensors comprises fewer than 10 photosensors. The linear array of photosensors may comprise fewer than 5 photosensors, for example 4, 3 or 2 photosensors. Two photosensors can provide measurements with two degrees of freedom and so can be used when there is also a nitrogen dioxide sensor. At least three photosensors are required where the further signal is a third measured ultraviolet light signal.

The dispersive optical element is typically an optical interference filter, for example an optical interference band pass filter. Optical interference band pass filters allow light (in this case, ultraviolet light) of a selected wavelength band to pass through parallel to the axis, but they allow light of other wavelengths to pass through at an angle to the axis, providing a convenient mechanism to direct light of different wavelengths onto different photosensors in the linear array of photosensors. Preferably, the optical interference filter has a bandwidth of less than 5 nm, more preferably, less than 3.5 nm.

It is of particular benefit that the measurement and reference ranges employed by the invention fall into a limited wavelength range. This has enabled a gas analyser to be built which requires measurement of only a limited range of wavelength, for example, with a relatively simple construction using an optical interference filter and a linear array of photosensors.

Therefore, preferably the processor takes into account measured light signals (whether ultraviolet light signals or otherwise) which are indicative of sensed ultraviolet light in a range of no more than 80 nm (or no more than 60 nm). The detector may be sensitive to ultraviolet light within a range of no more than 80 nm (or no more than 60 nm, or no more than 30 nm).

The processor may, for example, be a microprocessor, microcontroller or electronic circuit.

Preferably, the photosensors measure ultraviolet light across a substantially continuous range of wavelengths including the measurement range and the reference range or ranges which the first and second (and third, if present) measured ultraviolet light signals concern. The photosensors are preferably sensitive to ultraviolet light across at least 85% of the wavelength range including and extending between the measurement range or ranges, and the reference range or ranges.

Where a dispersive optical element is employed, the position on the linear array of photosensors where light of a particular wavelength falls may vary with temperature, as a result of thermal expansion. This causes the relative proportion of light in each measurement band and reference band which falls on individual photosensors to change. The relative proportion of light in each measurement band and reference band which falls on each photosensor at different temperature may be measured and stored in a look-up table. It may be that the gas analyser further comprises a temperature sensor and the processor is configured (e.g. programmed) to take into account the measured temperatures when generating the measurement output signal. Thus, the processor may be configured (e.g. programmed) to take into account changes in the relative proportion of light in each measurement band and reference band which falls on each photosensor, with temperature measured by the temperature sensor.

According to a second aspect of the invention there is provided a gas analyser for measuring the concentration of a target analyte, the gas analyser comprising a sample chamber in gaseous communication with ambient air, at least one light source, a detector configured to receive light emitted by the at least one light source and passed through the sample chamber, and a processor, the detector comprising a dispersive optical element and a linear array of photosensors (e.g. photodiodes) configured so that light from the at least one light source is separated by wavelength by the dispersive optical element and directed onto the linear array of photosensors such that each photosensor receives light at a different range of wavelengths, each photosensor operable to output a measured light signal indicative of light sensed by the photosensor, the plurality of measured light signals including at least a first measured light signal indicative of sensed light in at least some of a measurement range of wavelengths, and a second said measured light signal indicative of sensed light in at least some of a reference range of wavelengths, wherein the processor is configured (e.g. programmed) to generate a measurement output signal indicative of the concentration of the target analyte in ambient air taking into account the first and second measured light signals.

The plurality of measured light signals may include a third said measured light signal indicative of sensed light in at least some of a further reference range of wavelengths, and wherein the processor is configured (e.g. programmed) to generate a measurement output signal indicative of the concentration of the target analyte in ambient air taking into account the first, second and third measured light signals. Therefore, it may be that the linear array of detectors comprises at least three detectors.

Preferably, the target analyte is formaldehyde and the at least one light source is at least one ultraviolet light source. However, for the second and fourth aspects of the invention, the target analyte may be another gaseous analyte, for example CO, $CO_2$, $O_2$ or $H_2S$, and the at least one light source may be an infrared light source.

Preferably, in embodiments where the target analyte is formaldehyde and the at least one light source is at least one ultraviolet light source, the at least first measured light signal is indicative of sensed light in at least some of a measurement range of 337.5 nm to 346 nm or 325 nm to 332 nm, and the second said measured light signal is indicative of sensed light in at least some of one of a reference range of 332 nm to 337 nm, 347 nm to 350 nm or 356 nm to 370 nm, and the third said measured ultraviolet light signal is indicative of sensed light in at least some of another of the reference ranges of 332 nm to 337 nm, 347 nm to 350 nm or 356 nm to 370 nm.

It may be that the dispersive optical element is an optical interference band pass filter.

It may be that the gas analyser comprises a collimator located between the at least one light source and the sample chamber so that light from the at least one light source is substantially parallel while it passes through the sample chamber. The collimator may comprises a spherical lens.

Typically, the gas analyser comprises a lens which substantially focuses light from the detector, that has passed through the sample chamber, onto the dispersive element (e.g. optical interference band pass filter). Said lens may be a spherical lens. The said lens may focus substantially parallel light from the collimator, which has passed through the sample chamber. The light transmitted by the dispersive element has a wavelength which varies with orientation and the linear array of photosensors is spaced apart from the dispersive element, meaning that light of different (albeit in some embodiments overlapping) ranges of wavelengths falls onto different photosensors in the linear array. However, due to the focussing, the light from the detector passes through a relatively small part of the dispersive element and so the light falling on each photosensor comes from a smaller range of angles and so a narrower range of wavelengths, than would be the case if light from the sample chamber was not focussed onto the dispersive element.

Typically, the light transmitted by the dispersive element is not redirected by a further lens, at least in the plane of the linear array of photosensors, before it falls onto the linear array of photosensors. In an example embodiment it is focussed in a plane orthogonal to the linear array of photosensors by a circular lens.

The gas analyser may further comprise a temperature sensor, wherein the processor is configured to take into account the measured temperatures when generating the measurement output signal. The processor may be configured (e.g. programmed) to take into account changes in the relative proportion of light in each measurement band and reference band which falls on each photosensor, with temperature measured by the temperature sensor.

The linear array of photodiodes may comprise fewer than 10 photodiodes.

It may be that the detector is sensitive to ultraviolet light within a range of no more than 80 nm.

Further optional features of the second aspect of the invention are described above with reference to the first aspect of the invention.

According to a third aspect of the invention there is provided a method of measuring the concentration of formaldehyde in ambient air within an enclosed environment comprising the steps of;

(i) providing a gas analyser comprising at least one ultraviolet light source, a sample chamber in gaseous communication with ambient air and at least one detector, the detector comprising at least one photosensor;

(ii) the at least one photosensor detecting light from the at least one ultraviolet light source that has passed through the sample chamber to produce a plurality of measured ultraviolet light signals including at least a first measured ultraviolet signal indicative of sensed ultraviolet light in at least some of a measurement range of 337.5 nm to 346 nm or 325 nm to 332 nm, and a second said measured ultraviolet light signal indicative of sensed ultraviolet light in at least some of a reference range of 332 nm to 337 nm, 347 nm to 350 nm or 356 nm to 370 nm; and (iii) generating a measurement output signal indicative of the concentration of formaldehyde in ambient air taking into account the first and second measured ultraviolet light signals and at least one further signal which is dependent on the concentration of nitrogen dioxide in ambient air and at least partially independent of the first and second measured ultraviolet light signals.

Preferably, the gas analyser comprises a nitrogen dioxide sensor in gaseous communication with ambient air and wherein the further signal is an output of the nitrogen dioxide sensor representative of the concentration of nitrogen dioxide in ambient air.

The further signal may be a third measured ultraviolet signal indicative of sensed ultraviolet light in at least some of the further reference range of 332 nm to 337 nm, 347 nm to 350 nm or 356 nm to 370 nm.

Further optional features of the third aspect of the invention are described above with reference to the first and second aspects of the invention.

According to a fourth aspect of the invention, a method of measuring the concentration of a target analyte comprising the steps of;

(i) providing a gas analyser comprising a sample chamber in gaseous communication with ambient air, at least one light source, a detector configured to receive light emitted by the at least one light source and passed through the sample chamber, the detector comprising a dispersive optical element and a linear array of photosensors;

(ii) directing light from the light source through the sample chamber and the dispersive optical element onto the photosensors of the linear array of photosensors, such that the range of wavelengths of light received by each photosensor is dependent on the position of that photosensor in the linear array of photosensors as a result of dispersion of the light by the dispersive optical element;

(iii) the photosensors producing a plurality of measured light signals including at least a first measured light signal indicative of sensed light in at least some of a measurement range of wavelengths, and a second said measured light signal indicative of sensed light in at least some of a reference range of wavelengths; and (iv) generating a measurement output signal indicative of the concentration of the target analyte in ambient air taking into account the first and second measured light signals.

Preferably, the plurality of measured light signals includes a third said measured light signal indicative of sensed light in at least some of a further reference range of wavelengths, and a measurement output signal indicative of the concentration of the target analyte in ambient air is generated taking into account the first, second and third measured light signals.

The first and second reference range of wavelengths are not overlapping ranges of wavelengths.

Preferably, the target analyte is formaldehyde and the at least one light source comprises at least one ultraviolet light source.

Preferably, in embodiments where the target analyte is formaldehyde and the at least one light source is at least one ultraviolet light source, the first measured light signal is indicative of sensed light in at least some of a measurement range of 337.5 nm to 346 nm or 325 nm to 332 nm, and the second said measured light signal is indicative of sensed light in at least some of one of a reference range of 332 nm to 337 nm, 347 nm to 350 nm or 356 nm to 370 nm, and the third said measured light signal is indicative of sensed light in at least some of another of the reference ranges of 332 nm to 337 nm, 347 nm to 350 nm or 356 nm to 370 nm.

The gas analyser may comprise a temperature sensor and the processor may determine which signals from the photosensors correspond to which of the at least first, second and third measured ultraviolet light signals at the measured temperature.

Further optional features of the fourth aspect of the invention are described above with reference to the first, second and third aspects of the invention.

DESCRIPTION OF THE DRAWINGS

An example embodiment of the present invention will now be illustrated with reference to the following Figures in which.

DETAILED DESCRIPTION OF AN EXAMPLE EMBODIMENT

First Embodiment

Figure 1:
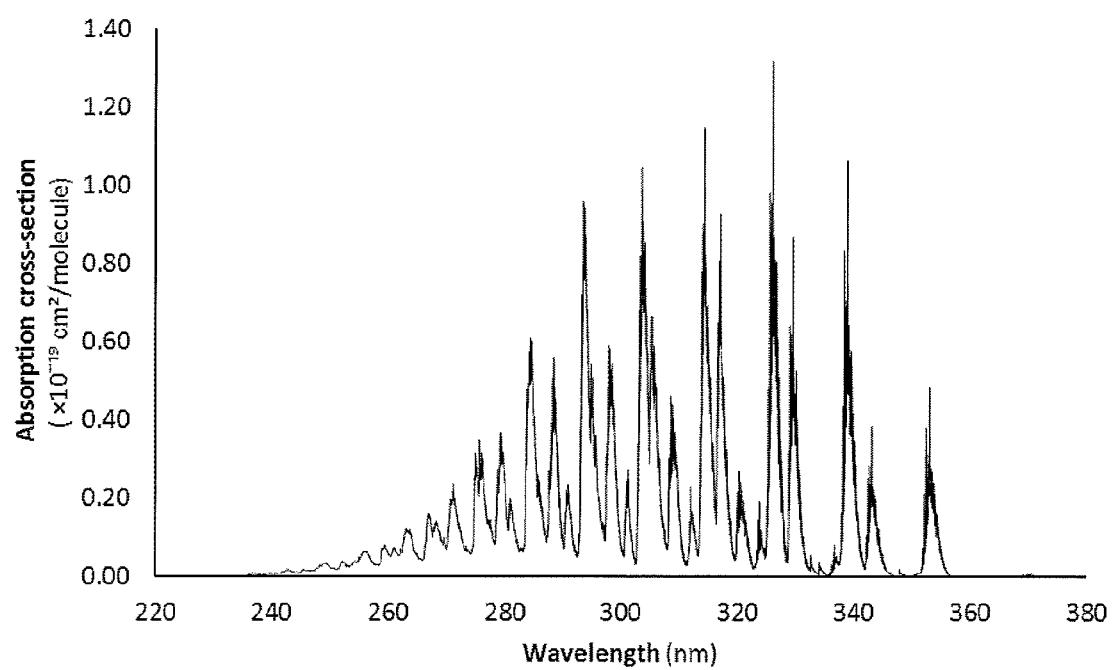
FIG. 1 is an absorption spectrum for formaldehyde in the ultraviolet region of the spectrum.
Figure 2:
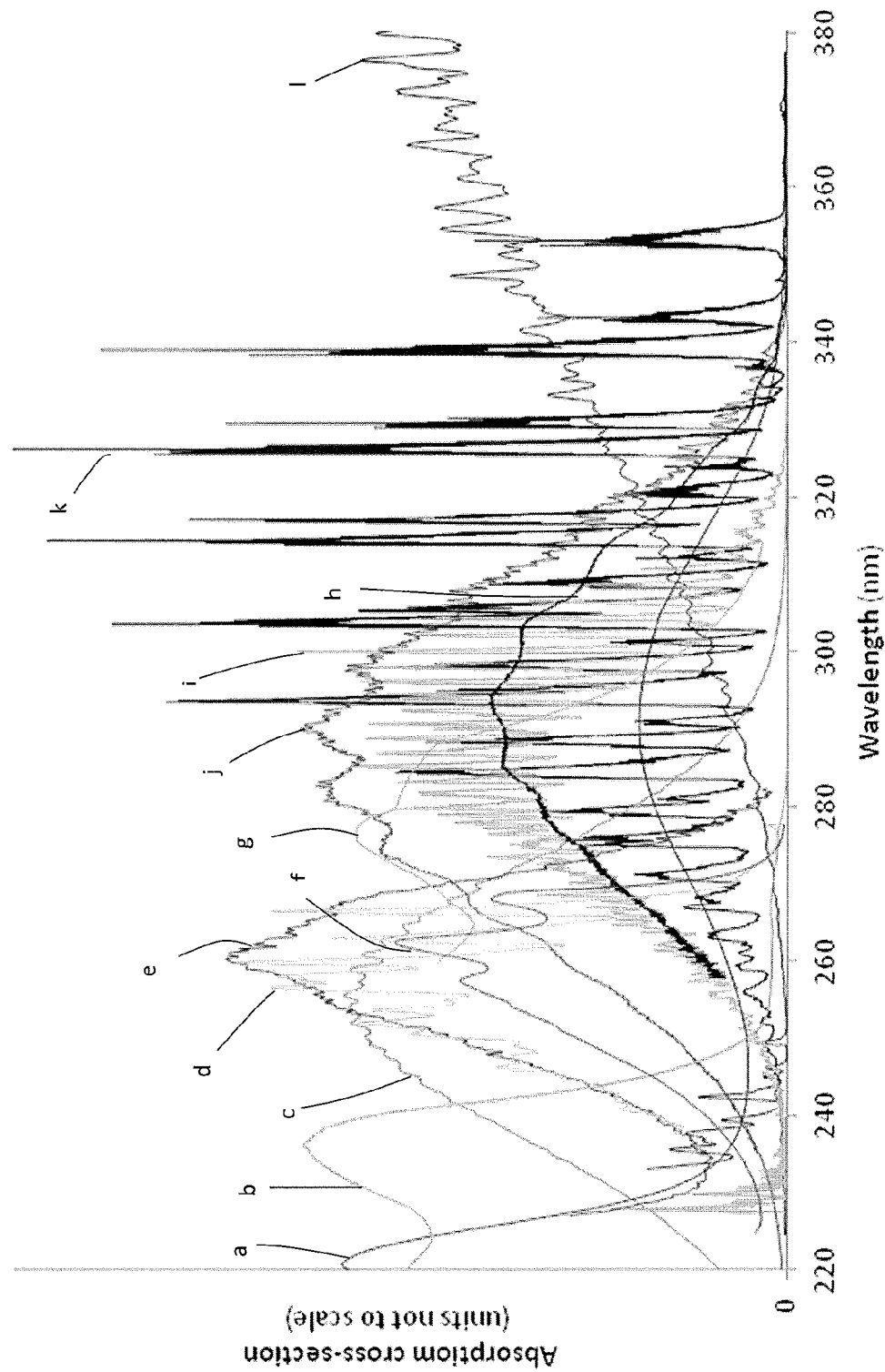
FIG. 2 is an absorption spectrum for gases commonly present within confined spaces within buildings that absorb light strongly within the ultraviolet region of the spectrum (a) decanal, (b) dichlorodiphenyltrichloroethane, (c) ozone, (d) ethylbenzene, (e) toluene, (f) triphenylphosphate, (g) dibutylphthalate, (h) hexanal, (i) sulphur dioxide, (j) acetaldehyde, (k) formaldehyde, (l) nitrogen dioxide.
Figure 3:
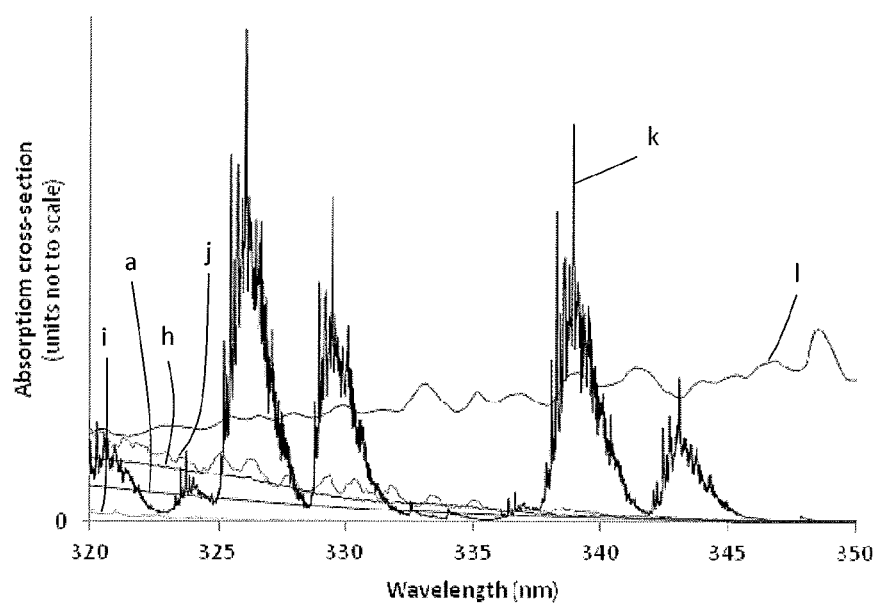
FIG. 3 is an absorption spectrum for gases commonly present within confined spaces within buildings within the range of wavelengths of 320 nm to 350 nm.

With reference to FIGS. 1 to 3, formaldehyde absorbs radiation within the ultraviolet region of the spectrum, specifically at various wavelengths within the range of wavelengths 260 nm to 355 nm (FIG. 1). Other gases potentially found within the ambient air within a building also absorb light within this region of the spectrum (interferents), such as acetaldehyde, ethylbenzene, nitrogen dioxide ($NO_2$), hexanal, ozone, decanal, dibutlyphthalate, sulphur dioxide, toluene, dichlorodiphenyltrichloroethane (DDT) and triphenylphosphate (see FIG. 2).

The inventors have discovered that measuring the intensity of light within the range of 330 nm to 350 nm allows them to avoid the majority of the above referenced interferents and to measure the concentration of formaldehyde accurately whilst taking into account the emission characteristics of the light source, and the concentration of the sole major interferent in this region of the spectrum, $NO_2$ (see FIG. 3).

Figure 4A:
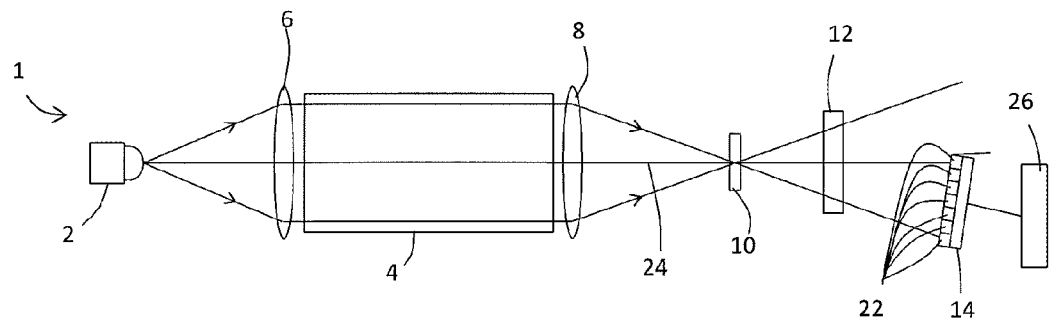
FIG. 4 is a ray trace diagram of (a) a gas sensor with an off-axis photodiode array and (b) an enlarged view of the range of angles transmitted by the filter incident on the off-axis photodiode array.
Figure 4A:
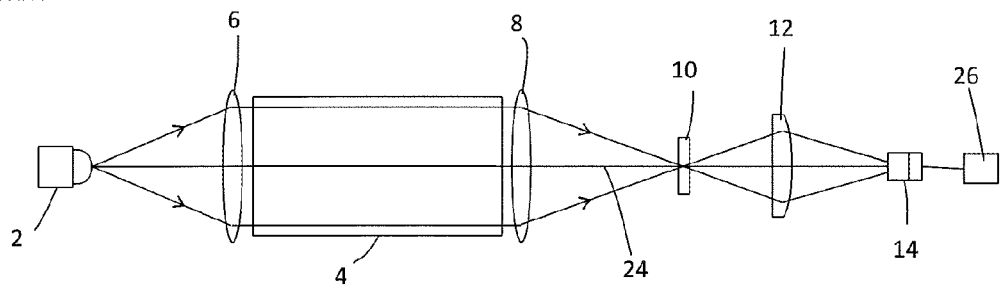

With reference to FIG. 4a, a first embodiment according to the invention is described. A gas analyser 1 for measuring the concentration of formaldehyde in ambient air within an enclosed environment comprises an ultraviolet light emitting diode (LED) 2 (acting as an ultraviolet light source), a sample chamber 4, a first spherical lens 6 with a focal length of 40 mm, a second spherical lens 8 with a focal length of 60 mm, a laser line filter 10 designed to transmit radiation approximately 1 nm either side of 355 nm to give a transmission range of 354 nm to 356 nm (acting as a dispersive optical element), a cylindrical lens with a focal length of 60 mm 12 and a linear photodiode array (acting as a detector) 14.

The gas analyser comprises a body 16 that houses the above components. The body comprises a gas permeable membrane 18 spanning an aperture 20 within the body. The gas permeable membrane allows gaseous species from the environment surrounding the gas analyser to diffuse into the sample chamber whilst preventing particulates such as dust particles from entering the sample chamber.

The first and second spherical lens and the cylindrical lens are made from fused silica, a material that is transparent to ultraviolet radiation.

Figure 4B:
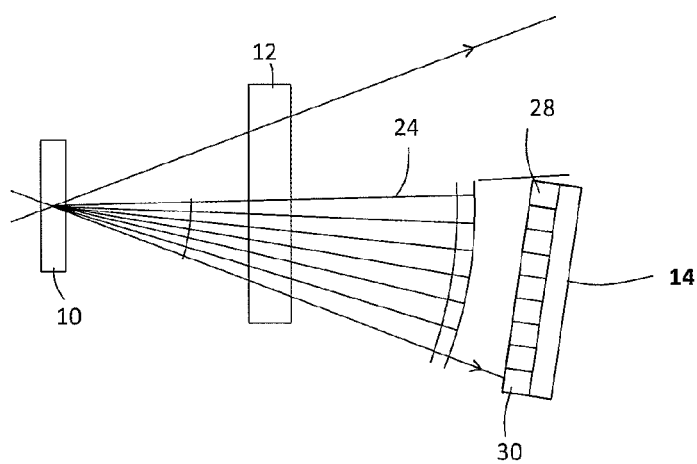

With reference to FIG. 4b, the photodiode array comprises a linear arrangement of nine photodiodes (acting as photosensors) 22 sensitive to ultraviolet radiation. Each photodiode within the photodiode array is 0.9 mm wide and separated from its neighbour by a separation of 0.1 mm such that the photodiode array is 8.9 mm wide. The photodiode array is located to one side of the main axis 24 of the ultraviolet light transmitted by the laser line filter and angled such that radiation transmitted by the laser line filter is incident substantially normal to the photodiode array.

The gas analyser comprises a processor 26 in electrical communication with each photodiode within the photodiode array.

The radiation incident normal to the laser line filter will only be transmitted if the wavelength of the radiation is within the range of 354 nm to 356 nm (that is, within 1 nm either side of the central wavelength 355 nm). However, the wavelength transmitted varies as the angle of incidence of the radiation moves away from zero (normal incidence) according to equation 1:

$$\lambda = \lambda_0 (1 - (n_0/n_f)^2 \sin^2\theta)^{1/2} \qquad (1)$$

where $\lambda$ is the wavelength of light transmitted, $\lambda_0$ is the original central wavelength transmitted by the laser line filter (355 nm in this example), $n_0$ is the refractive index of air (1.0), $n_f$ is the refractive index of the filter (1.74) and $\theta$ is the angle of incidence.

Figure 5:
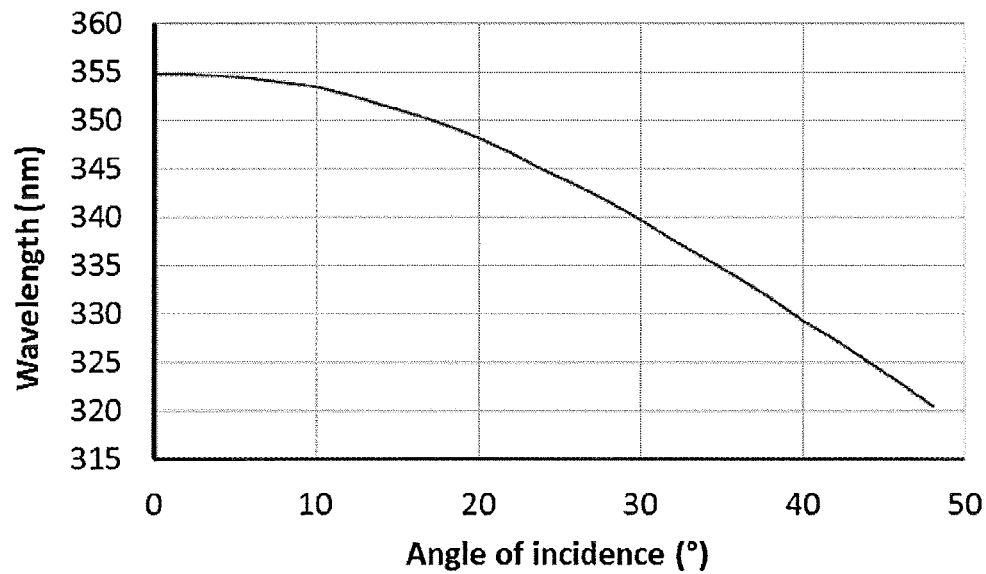
FIG. 5 is a plot of wavelength of light transmitted by the filter as a function of angle of incidence.

The dependence of the wavelength of radiation transmitted by the laser line filter on the angle of incidence is shown in FIG. 5. The photodiode array is arranged such that the wavelength of light incident to the photodiode array varies spatially across the photodiode array. Accordingly, the first photodiode within the photodiode array, 28, is arranged adjacent to the main axis of the gas analyser and the wavelength of light that is detected by the first photodiode is substantially within the wavelength range of 354 nm to 356 nm. The final photodiode within the photodiode array, 30, is arranged at an angle of approximately 40 degrees from the main axis of the gas analyser and the wavelength of light that is detected by the final photodiode is substantially within the wavelength range of 327 nm to 330 nm.

Generally, the photodiodes within the photodiode array produce a signal related to the intensity of ultraviolet light that is incident to them equally across the range of wavelengths emitted by the ultraviolet LED. That is, the photodiodes within the photodiode array are not sensitive to any one specific subset of the range of wavelengths that are received by the photodiode array. The photodiode array detects light continuously across the wavelength range of 355 nm to 325 nm. The photodiodes within the photodiode array are arranged such that there are minimal gaps between individual photodiodes within the photodiode array within which the intensity of ultraviolet light is not detected.

Typically, the gas analyser is fixed to the ceiling within a building such the ambient air of the building may diffuse into the sample chamber through the gas permeable membrane.

During use, ultraviolet light is emitted by the ultraviolet LED and collimated by the first spherical lens before passing through the sample chamber. Gases within the sample chamber including formaldehyde and any $NO_2$ or other interferents attenuate the intensity of light by absorption such that the intensity of light leaving the sample chamber is reduced.

The collimated light leaving the sample chamber is focussed by the second spherical lens onto the laser line filter such that the light incident to the laser line filter is incident at a range of angles.

Figure 6:
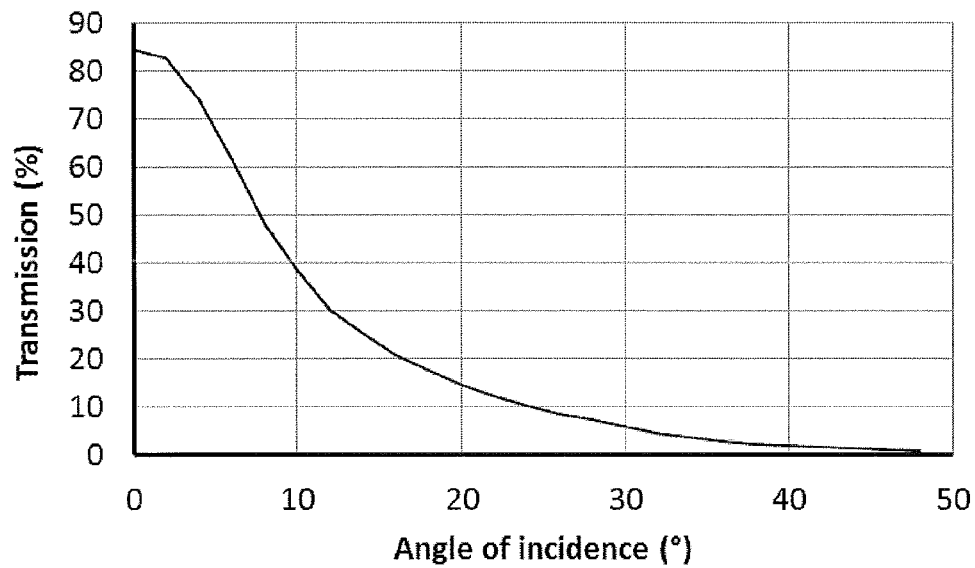
FIG. 6 is a plot of transmission of light by the filter as a function of angle of incidence.

With reference to FIGS. 5 and 6, as discussed above, the laser line filter transmits light depending on the wavelength of the incident light, and the wavelength of light transmitted by the laser line filter is dependent on the angle of incidence according to equation 1. At normal incidence, the laser line filter transmits light within the range of 354 nm to 356 nm. As the angle of incidence increases, the wavelength transmitted by the laser line filter decreases such that light transmitted by the laser line filter that had an angle of incidence of 30 degrees to the laser line filter has a wavelength of approximately 340 nm, for example.

Each photodiode within the photodiode array produces a signal representative of the intensity of light incident upon it and therefore the photodiode array produces a plurality of outputs which are together representative of the intensity of light incident upon the photodiode array as a whole.

In addition, the signal produced by each photodiode within the photodiode array is also indicative of the intensity of the specific range of wavelengths incident to that individual photodiode. Therefore, the continuous range of wavelengths that is incident on the photodiode array may be broken up into specific wavelength ranges that coincide with an absorption peak of the target analyte formaldehyde, and specific wavelength ranges within which the target analyte formaldehyde does not absorb.

Formaldehyde has absorption peaks at the range of wavelengths of 337.5 nm to 346 nm and 325 nm to 332 nm. In the current embodiment, the signal produced by the photodiodes within the photodiode array that receive light within the range 337.5 nm to 346 nm (the fourth and fifth photodiodes) is combined by the processor to form a first output (acting as a first measured ultraviolet signal).

Formaldehyde does not absorb significantly within the range of wavelengths of 332 nm to 337 nm and 347 nm to 350 nm. The signals produced by the photodiodes within the photodiode array that receive light within the range of wavelengths 332 nm to 337 nm (the sixth and seventh photodiodes) are received by the processor and combined to form a second output (acting as a second measured ultraviolet signal), and the signals produced by the photodiodes within the photodiode array that receive light within the range of wavelengths 347 nm to 350 nm (the second and third photodiodes) are received by the processor and combined to form a third output (acting as one further signal dependent on the concentration of $NO_2$ in ambient air).

The three produced outputs provide three independent measurements of the intensity of light. The processor calculates three independent variables of the system from the three outputs. These variables are the fluctuation in the intensity of light emitted by the ultraviolet LED, the concentration of the target analyte formaldehyde, and the concentration of any interferent analyte or analytes present in the gas sample chamber that also absorb to a significant extent in the ultraviolet range of wavelengths.

Accordingly, the first output is calibrated by the second and third outputs to account for any fluctuations in the intensity of light emitted by the ultraviolet light source and for the presence of any interferent analytes in the gas sample chamber, to produce a final output (acting as a measurement output signal) related to the concentration of the target analyte formaldehyde.

With reference to FIG. 3, the main potential interferent analyte present in indoor environments is $NO_2$, which absorbs relatively strongly throughout the region of the spectrum measured in the above mentioned ranges of wavelengths. $NO_2$ absorption changes across this range of wavelengths in an approximately linear manner. Therefore, a measurement of the $NO_2$ concentration at a first wavelength allows the absorption of light at a second wavelength due to the presence of $NO_2$ to be determined without requiring a second measurement.

Accordingly, measuring the intensity of light within two ranges of wavelengths where the target analyte formaldehyde does not absorb (332 nm to 337 nm and 347 nm to 350 nm) and where the only significant absorption is due to the presence of $NO_2$, allows both the reduction in the intensity of light due to the presence of $NO_2$ and changes in the intensity of light due to fluctuations in the intensity of light emitted by the ultraviolet LED to be accounted for. Therefore, a calibrated concentration of formaldehyde present can be measured, even in the presence of an interferent.

Figure 7:
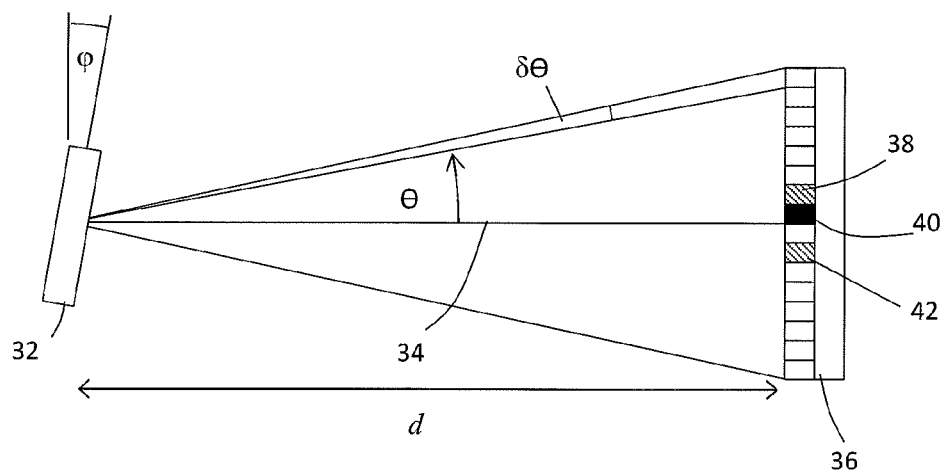
FIG. 7 is a plan view of a gas sensor according to one embodiment of the invention.

In an alternative embodiment, with reference to FIG. 7, the laser line filter 32 is set at an angle φ to the main axis 34 and the photodiode array 36 comprises sixteen photodiodes and is positioned centrally on the main axis at a distance d from the centre of the laser line filter. Light is received by each photodiode from a range of angles δθ of approximately 3.6°. In this embodiment the first output 38 is measured by the seventh photodiode and second output 40 is measured by the eighth photodiode, and the third output 42 is measured by the tenth photodiode.

Second Embodiment

In an alternative embodiment, the range of wavelengths of light received by the second and third photodiodes within the photodiode array of the first embodiment is 351 nm to 345 nm. The range of wavelengths received by the fourth and fifth photodiodes within the photodiode array is 347 nm to 336 nm. The range of wavelengths received by the sixth and seventh photodiodes within the photodiode array is 338 nm to 331 nm.

Therefore, the first output produced from the signals from the fourth and fifth photodiodes corresponds to the intensity of light that is absorbed by formaldehyde (having a wavelength range of 346 nm to 337.5 nm) and to light that is not absorbed by formaldehyde (having a wavelength of 337 nm and 347 nm). Accordingly, the first output contains a major component that is related to the concentration of the target analyte formaldehyde and minor components that are not related to the concentration of the target analyte formaldehyde. That is, the first output of the current embodiment contains components of the first, second and third outputs of the first embodiment.

Similarly, the second output produced by the signals from the sixth and seventh photodiodes contains a major component that is independent to the concentration of the target analyte formaldehyde (wavelengths 337 nm to 332 nm), and a minor component that is dependent on the concentration of the target analyte formadehyde (wavelength of 338 nm), and the third output produced by the signals from the second and third photodiodes contains a major component that is independent to the concentration of the target analyte formaldehyde (wavelengths 351 nm to 347 nm), and a minor component that is dependent on the concentration of the target analyte formaldehyde (wavelengths 345 nm to 346 nm).

However, whilst the components of the three outputs is more complex than those produced in the first embodiment, there are still three variables (the concentration of formaldehyde, the concentration of $NO_2$ and a measure of the intensity of light emitted by the ultraviolet LED) and three at least partially independent measurements, therefore allowing the processor to calculate the components of the three outputs to arrive at values that correspond to the first to third outputs of the first embodiment, and to produce a calibrated final output that is directly related to the concentration of formaldehyde in the sample chamber.

For example, the outputs for the first and second embodiments may correspond generally to the following equations:

First Embodiment $$x_1 = A \times D$$

$$x_2 = B \times D$$

$$x_3 C \times D \quad (2)$$

where $x_1$ is the first output, $x_2$ is the second output, $x_3$ is the third output, A is related to the intensity of light within the range of wavelengths 346 nm to 337.5 nm, B is related to the intensity of light within the range of wavelengths 337 nm to 332 nm, C is related to the intensity of light within the range of wavelengths 350 nm to 347 nm and D is a scaling constant dependent on the instantaneous brightness of the ultraviolet LED.

Second Embodiment $$x_1 = (a_1 A + b_1 B + c_3 C) \times D$$

$$x_2 = (a_2 A + b_2 B) \times D$$

$$x_3 = (a_3 A + c_3 C) \times D \quad (3)$$

where $x_1$, $x_2$, $x_3$, A, B, C and D are as per the first embodiment, and where $a_1$, $a_2$ and $a_3$ are weightings of the proportion of A in each of $x_1$, $x_2$ and $x_3$ respectively, $b_1$ and $b_2$ are weightings of the proportion of B in each of $x_1$, $x_2$ respectively, and $c_1$ and $c_3$ are weightings of the proportion of C in each of $x_1$ and $x_3$ respectively.

Third Embodiment

In a third embodiment the photodiode array of the gas analyser comprises three photodiodes (acting as photosensors). Each photosensor receives light from a separate range of wavelengths. The first photodiode within the photodiode array receives light within the range of wavelengths 347 nm to 350 nm, the second photodiode receives light within the range of wavelengths 337.5 nm to 346 nm and the third photodiode receives light within the range of wavelengths 332 nm to 337 nm. Accordingly, the signal produced by the first photodiode received by the processor corresponds to the third output, the signal produced by the second photodiode received by the processor corresponds to the first output and the signal produced by the third photodiode received by the processor corresponds to the second output.

Therefore, the processor calculates the measured concentration of formaldehyde within the sample chamber directly from the signals produced by the first to third photodiodes within the photodiode array.

In alternative embodiments, each photodiode receives light through a separate filter to ensure that each photodiode receives light within the desired range of wavelengths. The first photodiode receives light through a first filter that only transmits light within the range of wavelengths 337.5 nm to 346 nm, the second photodiode receives light through a second filter that only transmits light within the range of wavelengths 332 nm to 337 nm Fourth Embodiment In another embodiment, the gas analyser of either the first and second embodiments further comprises a temperature sensor.

The optical properties of the components of the gas analyser vary with temperature. Accordingly, the degree to which the wavelength of light incident on the photodiode array varies spatially across the photodiode array varies with temperature. For example, for the gas analyser of the first embodiment, at a first temperature, the second and third photodiodes receive light that corresponds to the second output, the fourth and fifth photodiodes receive light that corresponds to the first output and the sixth and seventh photodiodes receive light that corresponds to the third output. At a second temperature, the third and fourth photodiodes receive light that corresponds to the second output, the fifth and sixth photodiodes receive light that corresponds to the first output and the seventh and eighth photodiodes receive light that corresponds to the third output. Therefore, it is necessary for the processor to adjust which signals from which photodiodes are to be combined to form the first, second and third outputs.

During use, the temperature sensor measures the temperature of the gas analyser and produces a signal that is related to the temperature of the gas analyser, which is received by the processor. The processor refers to a look up table that stores which photodiode signals correspond to which output at a given temperature, and determines the identity of the photodiodes within the photodiode array that are receiving light that correspond to the first, second and third outputs at the measured temperature, and then proceeds to produce the first to third outputs, process the said outputs and determine the concentration of the target analyte formaldehyde according to the previous embodiment.

Fifth Embodiment

Figure 8:
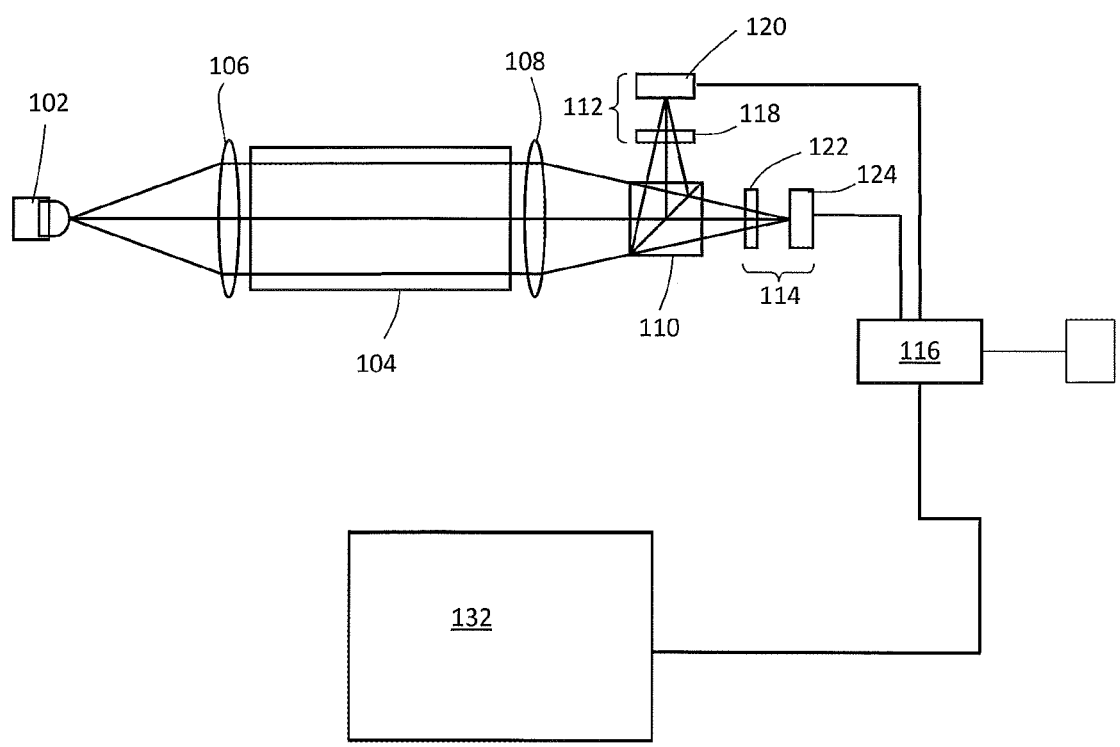
FIG. 8 is a plan view of a gas sensor according to one embodiment of the invention where an independent signal relating to the concentration of an interferent is obtained.

In a further embodiment with reference to FIG. 8, a gas analyser for measuring the concentration of formaldehyde in ambient air within a building comprises an ultraviolet light emitting diode (LED) 102 (acting as an ultraviolet light source), a sample chamber 104, a first spherical lens with a focal length of 40 mm 106, a second spherical lens with a focal length of 60 mm 108, a beamsplitter 110, a first detector 112, a second detector 114 and a processor 116.

Figure 9:
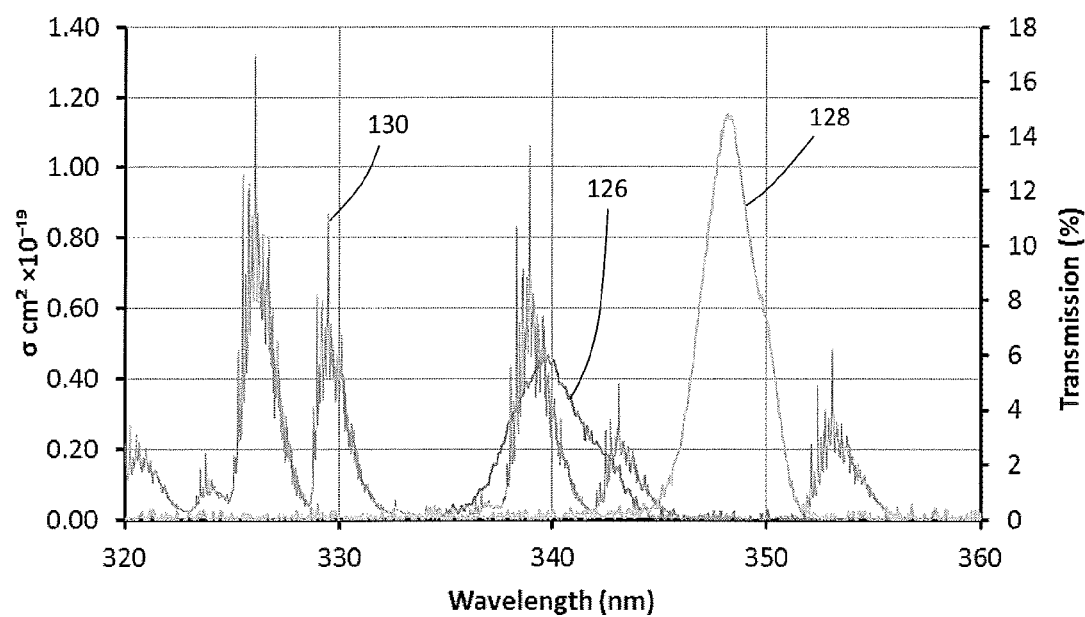
FIG. 9 shows where the measurement and reference range of wavelengths used for one embodiment of the invention are located and compared to the absorption spectrum for formaldehyde.

The first detector comprises a first filter 118 and a first photodiode 120 (acting as a photosensor), the first filter ensuring that only light within a range of wavelengths 346 nm to 337.5 nm reaches the first photodiode. The second detector comprises a second filter 122 and a second photodiode 124 (acting as a photosensor), the second filter ensuring that only light within a range of 337 nm to 332 nm reaches the second photodiode. In this case, the second spherical lens focuses light on the photodiodes rather than the interference filters. FIG. 9 shows the overlap of the range of wavelengths transmitted by the first filter 126 and the range of wavelengths transmitted by the second filter 128 with the absorption spectrum of formaldehyde 130.

During use, ultraviolet light is emitted by the LED, is collimated by the first spherical lens, passes through the sample chamber and is focussed by the second spherical lens. The light is then split between the first and second detector by the beamsplitter, where the intensity of light within the specified ranges of wavelengths is detected.

The signal produced by the first detector is related to the concentration of formaldehyde within the sample chamber, the concentration of $NO_2$ within the sample chamber and to the emission characteristics of the LED. The signal produced by the second detector is related to the concentration of $NO_2$ within the sample chamber and to the emission characteristics of the LED.

The gas analyser further comprises a standard independent electrochemical $NO_2$ detector 132. The electrochemical $NO_2$ detector produces a signal indicative of the concentration of $NO_2$ present at the working electrode of the detector. The signal from the electrochemical $NO_2$ detector is sent to the processor.

The processor calculates the concentration of $NO_2$ present in the ambient air surrounding the gas analyser from the signal produced by the electrochemical $NO_2$ sensor. The processor then subtracts the contribution to the signals of the first and second detectors due to the measured concentration of $NO_2$. The resulting adjusted signal from the second detector is used to calibrate the adjusted signal from the first detector to produce a final output indicative of the concentration of formaldehyde in the sample chamber.

In a further alternative embodiment, a gas analyser measures the intensity of ultraviolet light received by photosensors within the range of wavelengths 337.5 nm to 346 nm and within the range of wavelengths 332 nm to 337 nm according to the embodiments above. The two signals produced correspond to a signal related to the concentration of formaldehyde and any interferents within the sample chamber, and a signal related to the concentration of any interferents within the sample chamber and the instantaneous brightness of the light source. An independent electrochemical $NO_2$ sensor is provided, in addition to the gas analyser, to determine the $NO_2$ concentration in the ambient air. The independent electrochemical $NO_2$ sensor is in electrical communication with gas analyser in which a signal indicative of the concentration of $NO_2$ from the electrochemical gas analyser is received by the processor of the gas analyser to allow the contribution to the two signals produced the optical gas analyser due to the concentration of $NO_2$ to be subtracted.

Figure 10:
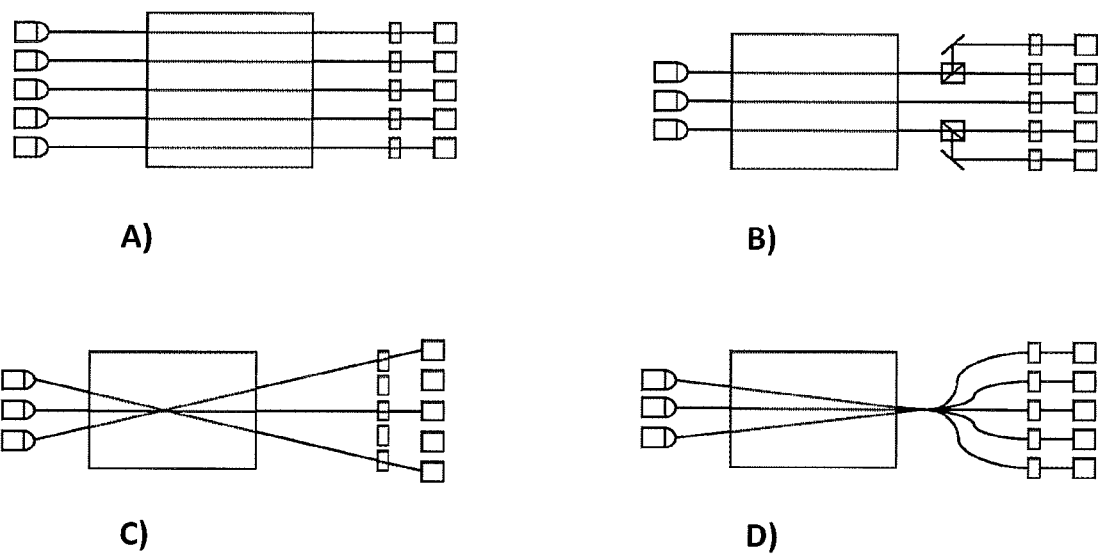
FIG. 10 is a plan view of alternative light source/detector arrangements.

With reference to FIG. 10 in further embodiments, the gas analyser comprises more than one light source and/or more than one detector. For example, in one embodiment the gas analyser comprises four ultraviolet light sources and four detectors.

Figure 11:
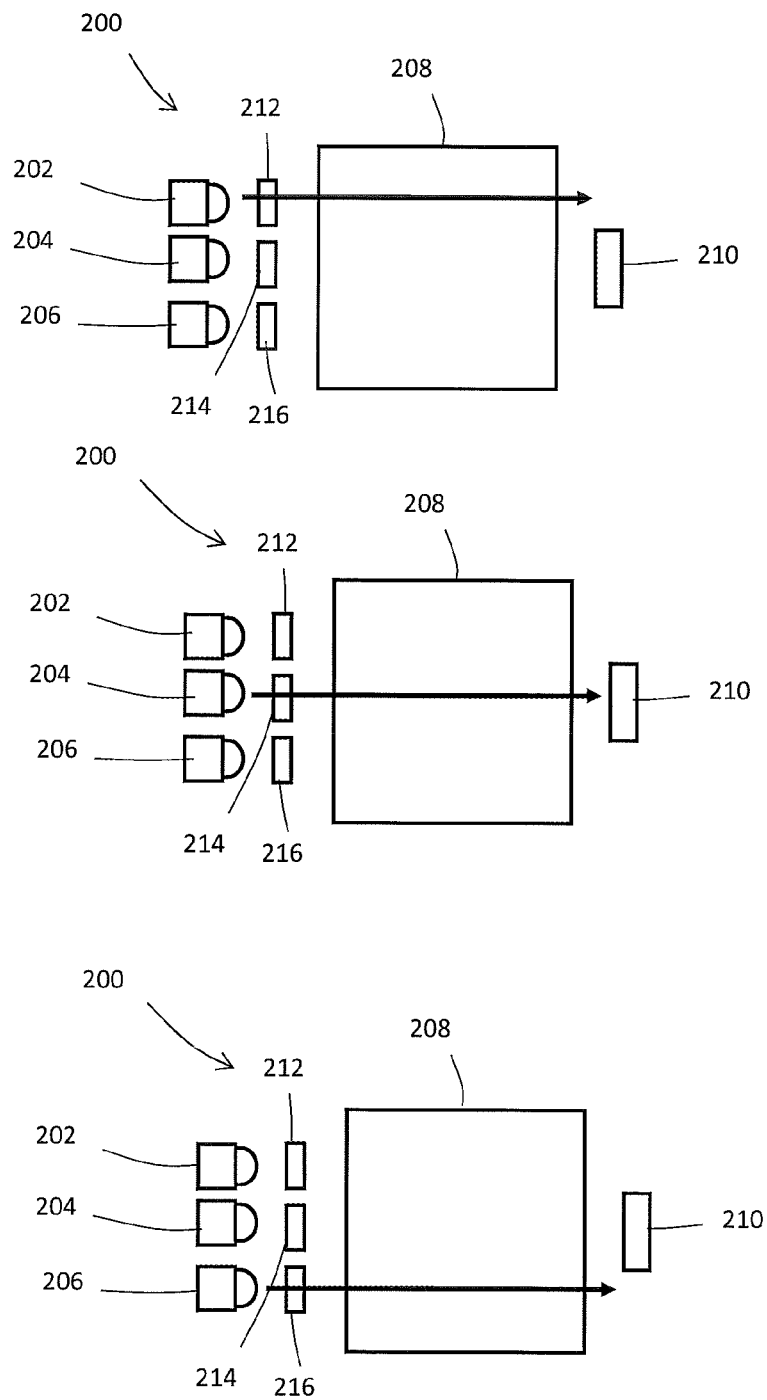
FIG. 11 is a schematic of an embodiment of the invention comprising three sequentially activated ultraviolet light sources are used with a single detector.

In another embodiment, with reference to FIG. 11, the gas analyser 200 comprises three ultraviolet light sources 202, 204 and 206, a sample chamber 208 and a single photodiode 210, where each ultraviolet light source has a separate filter and the wavelength of light transmitted by each filter is different. The first filter 212 transmits light within the range of wavelengths 337.5 nm to 346 nm, the second filter 214 transmits light within the range of wavelengths 332 nm to 337 nm and the third filter 216 transmits light within the range of wavelengths 247 nm to 350 nm. During use, the three ultraviolet light sources emit light sequentially so that the light detected by the photodiode corresponds to only a single wavelength range emitted by a single ultraviolet light source at any given time, so that the output of the photodiode forms the first, second and third measured ultraviolet light signals, separated in time.

Further variations and modifications may be made within the scope of the invention herein disclosed.

The invention claimed is:

1. A gas analyser for measuring the concentration of formaldehyde in ambient air within an enclosed environment, the gas analyser comprising a sample chamber in gaseous communication with ambient air, at least one ultraviolet light source, a detector configured to receive ultraviolet light emitted by the at least one ultraviolet light source and passed through the sample chamber, and a processor, the detector comprising at least one photosensor sensitive to ultraviolet light emitted by the at least one ultraviolet light source and operable to produce a plurality of measured ultraviolet light signals indicative of sensed ultraviolet light in each of a plurality of wavelength bands, the plurality of measured ultraviolet light signals including at least a first measured ultraviolet light signal indicative of sensed ultraviolet light in at least some of a measurement range of 337.5 nm to 346 nm or 325 nm to 332 nm, and a second said measured ultraviolet light signal indicative of sensed ultraviolet light in at least some of a reference range of 332 nm to 337 nm, 347 nm to 350 nm or 356 nm to 370 nm, wherein the processor is configured to generate a measurement output signal indicative of the concentration of formaldehyde in ambient air taking into account the first and second measured ultraviolet light signals and at least one further signal which is dependent on the concentration of nitrogen dioxide in ambient air and at least partially independent of the first and second measured ultraviolet light signals.

2. A gas analyser according to claim 1, further comprising a nitrogen dioxide sensor in gaseous communication with ambient air and wherein the further signal is an output of the nitrogen dioxide sensor representative of the concentration of nitrogen dioxide in ambient air.

3. A gas analyser according to claim 1, wherein the further signal is a third measured ultraviolet light signal indicative of sensed ultraviolet light in at least some of a further reference range of 332 nm to 337 nm, 347 nm to 350 nm or 356 nm to 370 nm.

4. A gas analyser according to claim 1, wherein the further signal is a third measured ultraviolet light signal indicative of sensed ultraviolet light in at least some of a further reference range of 332 nm to 337 nm, 347 nm to 350 nm or 356 nm to 370 nm.

5. A gas analyser according to claim 4, wherein (i) the second measured ultraviolet light signal is indicative of sensed ultraviolet light in at least some of a reference range of 332 nm to 337 nm and the third measured ultraviolet light signal is indicative of sensed ultraviolet light in at least some of the reference range of 347 nm to 350 nm; or (ii) the second measured ultraviolet light signal is indicative of sensed ultraviolet light in at least some of a reference range of 332 nm to 337 nm and the third measured ultraviolet light signal is indicative of sensed ultraviolet light in at least some of the reference range of 356 nm to 370 nm; or (iii) the second measured ultraviolet light signal is indicative of sensed ultraviolet light in at least some of a reference range of 356 nm to 370 nm and the third measured ultraviolet light signal is indicative of sensed ultraviolet light in at least some of the reference range of 347 nm to 350 nm.

6. A gas analyser according to claim 5, wherein (i) the second measured ultraviolet light signal is indicative of sensed ultraviolet light in at least some of a reference range of 332 nm to 337 nm and the third measured ultraviolet light signal is indicative of sensed ultraviolet light in at least some of the reference range of 347 nm to 350 nm and the processor does not use as a reference any measured ultraviolet light signal indicative of sensed ultraviolet light in the range of 356 nm to 370 nm or (ii) the second measured ultraviolet light signal is indicative of sensed ultraviolet light in at least some of a reference range of 332 nm to 337 nm and the third measured ultraviolet light signal is indicative of sensed ultraviolet light in at least some of the reference range of 356 nm to 370 nm and the processor does not use as a reference any measured ultraviolet light signal indicative of sensed light in the range of 347 nm to 350 nm; or (iii) the second measured ultraviolet light signal is indicative of sensed ultraviolet light in at least some of a reference range of 356 nm to 370 nm and the third measured ultraviolet light signal is indicative of sensed ultraviolet light in at least some of the reference range of 347 nm to 350 nm and the processor does not use as a reference any measured light in the range of 332 nm to 337 nm.

7. A gas analyser according to claim 1, wherein the first measured ultraviolet light signal is indicative of sensed ultraviolet light in at least some of the measurement range of 337.5 nm to 346 nm and none of the range of 325 nm to 332 nm.

8. A gas analyser according to claim 1, wherein the second measured ultraviolet light signal is indicative of sensed ultraviolet light in at least some of the reference range of 332 nm to 337 nm and wherein the processor does not use as a reference any measured ultraviolet light signal indicative of sensed ultraviolet light in the range of 347 nm to 350 nm or 356 nm to 370 nm.

9. A gas analyser according to claim 1, wherein the detector comprises a dispersive optical element and a linear array of photosensors configured so that ultraviolet light from the at least one ultraviolet light source is separated by wavelength by the dispersive optical element and directed onto the linear array of photosensors such that each photosensor receives ultraviolet light at a different range of wavelength.

10. A gas analyser according to claim 9, wherein the linear array comprises fewer than 10 photosensors.

11. A gas analyser according to claim 9, wherein the dispersive optical element is an optical interference band-pass filter.

12. A gas analyser according to claim 9, wherein the gas analyser further comprises a temperature sensor and the processor is configured to take into account the measured temperatures when generating the measurement output signal.

13. A gas analyser according to claim 1, wherein the processor takes into account measured light signals which are indicative of sensed ultraviolet light in a range of no more than 80 nm.

14. A gas analyser for measuring the concentration of a target analyte, the gas analyser comprising a sampler changer in gaseous communication with ambient air, at least one light source, a detector configured to receive light emitted by the at least one light source and passed through the sample changer, and a processor,
the detector comprising a dispersive optical element and a linear array of photosensors configured so that light from the at least one light source is separated by wavelength by the dispersive optical element and directed onto the linear array of photosensors such that each photosensor receives light at a different range of wavelengths, each photosensor operable to output a measured light signal indicative of light sensed by the photosensor,
the plurality of measured light signals including at least a first measured light signal indicative of sensed light in at least some of a measurement range of wavelengths, and a second said measured light signal indicative of sensed light in at least some of a reference range of wavelengths,
wherein the processor is configured to generate a measurement output signal indicative of the concentration of the target analyte in ambient air taking into account the first and second measured light signals, and
wherein the gas analyser further comprises a temperature sensor, wherein the processor is configured to take into account changes in the relative proportion of light in each measurement band and reference band which falls on each photosensor, with temperature measured by the temperature sensor.

15. A method of measuring the concentration of formaldehyde in ambient air within an enclosed environment comprising the steps of;
(i) providing a gas analyser comprising at least one ultraviolet light source, a sample chamber in gaseous communication with ambient air and at least one detector, the detector comprising at least one photosensor;
(ii) the at least one photosensor detecting light from the at least one ultraviolet light source that has passed through the sample chamber to produce a plurality of measured ultraviolet light signals including at least a first measured ultraviolet signal indicative of sensed ultraviolet light in at least some of a measurement range of 337.5 nm to 346 nm or 325 nm to 332 nm, and a second said measured ultraviolet light signal indicative of sensed ultraviolet light in at least some of a reference range of 332 nm to 337 nm, 347 nm to 350 nm or 356 nm to 370 nm; and
(iii) generating a measurement output signal indicative of the concentration of formaldehyde in ambient air taking into account the first and second measured ultraviolet light signals and at least one further signal which is dependent on the concentration of nitrogen dioxide in ambient air and at least partially independent of the first and second measured ultraviolet light signals.

16. A method according to claim 15, wherein the gas analyser comprises a nitrogen dioxide sensor in gaseous communication with ambient air and wherein the further signal is an output of the nitrogen dioxide sensor representative of the concentration of nitrogen dioxide in ambient air.

17. A method according to claim 15, wherein the further signal is a third measured ultraviolet signal indicative of sensed ultraviolet light in at least some of the further reference range of 332 nm to 337 nm, 347 nm to 350 nm or 356 nm to 370 nm.

18. A method of measuring the concentration of a target analyte comprising the steps of;
  (i) providing a gas analyser comprising a sample chamber in gaseous communication with ambient air, at least one light source, a detector configured to receive light emitted by the at least one light source and passed through the sample chamber, the detector comprising a dispersive optical element and a linear array of photosensors, and a temperature sensor;
  (ii) directing light from the light source through the sample chamber and the dispersive optical element onto the photosensors of the linear array of photosensors, such that the range of wavelengths of light received by each photosensor is dependent on the position of that photosensor in the linear array of photosensors as a result of dispersion of the light by the dispersive optical element;
  (iii) the photosensors producing a plurality of measured light signals including at least a first measured light signal indicative of sensed light in at least some of a measurement range of wavelengths, a second said measured light signal indicative of sensed light in at least some of a reference range of wavelengths and a third said measured light signal indicative of sensed light in at least some of a further reference range of wavelengths;
  (iv) the processor determining which signals from the photosensors correspond to which of the at least first, second and third measured ultraviolet light signals at a measured temperature; and
  (v) generating a measurement output signal indicative of the concentration of the target analyte in ambient air taking into account the first, second and third measured light signals.

19. A method according to claim 18, wherein the target analyte is formaldehyde and the at least one light source comprises at least one ultraviolet light source.

20. A method according to claim 19, wherein the first measured light signal is indicative of sensed light in at least some of a measurement range of 337.5 nm to 346 nm or 325 nm to 332 nm, and the second said measured light signal is indicative of sensed light in at least some of one of a reference range of 332 nm to 337 nm, 347 nm to 350 nm or 356 nm to 370 nm, and the third said measured light signal is indicative of sensed light in at least some of another of the reference ranges of 332 nm to 337 nm, 347 nm to 350 nm or 356 nm to 370 nm.

* * * * *